(12) United States Patent
Lou et al.

(10) Patent No.: US 9,345,444 B2
(45) Date of Patent: May 24, 2016

(54) CT PILOT IMAGE ACQUISITION METHOD AND CT DEVICE

(71) Applicant: Shenyang Neusoft Medical Systems Co., Ltd., Shenyang (CN)

(72) Inventors: Shanshan Lou, Shenyang (CN); Han Zheng, Shenyang (CN)

(73) Assignee: SHENYANG NEUSOFT MEDICAL SYSTEMS CO., LTD., Shenyang (CN)

( * ) Notice: Subject to any disclaimer, the term of this patent is extended or adjusted under 35 U.S.C. 154(b) by 179 days.

(21) Appl. No.: 14/142,963

(22) Filed: Dec. 30, 2013

(65) Prior Publication Data

US 2015/0023464 A1    Jan. 22, 2015

(30) Foreign Application Priority Data

Jul. 17, 2013   (CN) .......................... 2013 1 0301555

(51) Int. Cl.

| | |
|---|---|
| *A61B 6/00* | (2006.01) |
| *G06T 5/00* | (2006.01) |
| *G06T 11/00* | (2006.01) |
| *A61B 6/02* | (2006.01) |
| *A61B 6/03* | (2006.01) |
| *H04N 5/357* | (2011.01) |

(52) U.S. Cl.
CPC ............... *A61B 6/5258* (2013.01); *A61B 6/027* (2013.01); *A61B 6/488* (2013.01); *A61B 6/5205* (2013.01); *G06T 11/005* (2013.01); *A61B 6/032* (2013.01); *A61B 6/4078* (2013.01); *A61B 6/5223* (2013.01); *G06T 5/002* (2013.01); *G06T 11/003* (2013.01); *H04N 5/357* (2013.01)

(58) Field of Classification Search
CPC .......... A61B 6/00; A61B 6/027; A61B 6/488; A61B 6/52; A61B 6/5205; A61B 6/5211; A61B 6/5223; A61B 6/5258; H04N 5/217; H04N 5/30; H04N 5/32; H04N 5/357–5/365; G01T 1/36; G01T 9/6203; G06T 5/00; G06T 5/001; G06T 5/002; G06T 7/00; G06T 7/0002; G06T 7/0012; G06T 7/0014; G06T 11/00; G06T 11/003; G06T 11/005; G06T 11/008

USPC ............. 378/4–20, 62, 91, 98, 162, 165, 204, 378/210, 901

See application file for complete search history.

(56) References Cited

U.S. PATENT DOCUMENTS

2007/0237286 A1* 10/2007 Imai ....................... A61B 6/032
378/4
2009/0086888 A1* 4/2009 Hagiwara ............. G06T 11/006
378/20

(Continued)

FOREIGN PATENT DOCUMENTS

| CN | 101401726 A | 4/2009 |
| CN | 101427924 A | 5/2009 |

(Continued)

OTHER PUBLICATIONS

Linghong Zhou et al., "CT-Based Simulation in Radiation Therapy", 3 pages.

(Continued)

*Primary Examiner* — Anastasia Midkiff
(74) *Attorney, Agent, or Firm* — Kilpatrick Townsend & Stockton LLP

(57) ABSTRACT

A CT pilot image acquisition method and a CT device are provided. The method may include: performing a helical scan on a predetermined area to be scanned, so as to obtain scanning data; reconstructing a tomographic image based on the scanning data; performing, at a predetermined positioning angle, a parallel beam projection on the tomographic image by using a virtual parallel X-ray beam, so as to obtain projection data; and re-binning a CT pilot image at the predetermined positioning angle based on the projection data. Parallel beam projection is adopted to process the tomographic image, to obtain a pilot image without geometric distortions. The obtained pilot image can reflect an anatomical structure of human body accurately.

10 Claims, 4 Drawing Sheets

(56) References Cited

U.S. PATENT DOCUMENTS

2009/0202126 A1* 8/2009 Tang ................ A61B 6/032
 382/131
2012/0263359 A1 10/2012 Kimoto

FOREIGN PATENT DOCUMENTS

| CN | 102573640 A | 7/2012 |
| CN | 103164593 A | 6/2013 |

OTHER PUBLICATIONS

The second Office Action issued on May 21, 2015 regarding the Chinese priority patent application (Appl.No. 201310301555.5).

The 3rd Office Action issued on Oct. 29, 2015 regarding the Chinese priority patent application (Appl.No. 201310301555.5).

"Radiation Oncology Physics", Yimin Hu, Atomic Energy Press, Sep. 30, 1999. n

* cited by examiner

CT PILOT IMAGE ACQUISITION METHOD AND CT DEVICE

CROSS-REFERENCE TO RELATED APPLICATIONS

The present application claims priority to Chinese patent application No. 201310301555.5, filed on Jul. 17, 2013, and entitled "CT PILOT IMAGE ACQUISITION METHOD AND CT DEVICE", the entire disclosure of which is incorporated herein by reference.

TECHNICAL FIELD

The present disclosure generally relates to image processing technology, and more particularly, to a Computed Tomography (CT) pilot image acquisition method and a CT device.

BACKGROUND

Pilot images, which are commonly used in CT technology, are mainly used to roughly reflect anatomical structures of human organs and positions of large lesions, so as to assist doctors to scan and position. Commonly used scanning methods include single pilot image scanning or double pilot images scanning. Referring to FIG. 1, a schematic diagram of pilot image scanning is illustrated, which includes a CT gantry (1), an X-ray tube (2), a detector (3), a patient table (4), and a scanning object (5). In the process of pilot image scanning, the CT gantry is fixed, which means the X-ray tube and the detector are fixed, and the patient table which carries the scanning object moves forward or backward at a constant speed to obtain scanning data. The double pilot images scanning is similar to the single pilot image scanning. After scanning an anteroposterior pilot image of the scanning object (if the scanning object is a human body, scanning from the front side of the human body, which is perpendicular to the plane of the patient table in FIG. 1), a lateral pilot image is scanned (scanning from the lateral side of the human body, that is the arm side of the human body in FIG. 1). With a simple imaging principle and a fast imaging speed, the above mentioned scanning methods can basically meet the doctors' needs for scanning and positioning. However, geometric distortion exists in pilot images obtained by the above mentioned scanning methods.

SUMMARY

In the prior art, images obtained by double pilot images scanning can reflect structures of human body more accurate than images obtained by single pilot image scanning, and can basically meet the doctors' needs. However, the pilot images obtained by these two methods have geometric distortion, which leads to a deviation between the pilot images and the actual structure of the scanning object. Therefore, a CT pilot image acquisition method and a CT device are provided in this disclosure, to solve the technical problem of geometric distortion in the pilot images obtained in the prior art.

In order to solve the problems mentioned above, a CT pilot image acquisition method and a CT device are provided in this disclosure.

According to embodiments of the present disclosure, a CT pilot image acquisition method is provided. The method may include: performing a helical scan on a predetermined area to be scanned, so as to obtain scanning data; reconstructing a tomographic image based on the scanning data; performing, at a predetermined positioning angle, a parallel beam projection on the tomographic image by using a virtual parallel X-ray beam, so as to obtain projection data; and re-binning a CT pilot image at the predetermined positioning angle based on the projection data.

In some embodiments, re-binning a CT pilot image at the predetermined positioning angle based on the projection data may include: compositing an image based on the projection data to obtain a composited image; and defining the composited image as the CT pilot image at the predetermined positioning angle.

In some embodiments, the method may further include: performing a denoising process on the composited image to obtain a denoised image; and defining the denoised image as the CT pilot image at the predetermined positioning angle.

In some embodiments, the method may further include: after the helical scan is performed on a predetermined area to be scanned and the scanning data is obtained, performing a denoising process on the obtained scanning data to obtain denoised scanning data, and defining the denoised scanning data as a basis for reconstructing the tomographic image.

In some embodiments, a thickness of the tomographic image and a distance between adjacent tomographic images may be adjustable.

In some embodiments, a pitch adopted in performing the helical scan on the predetermined area to be scanned, may be adjustable.

According to embodiments of the present disclosure, a CT device is provided. The CT device may include: a scanning unit, adapted for performing a helical scan on a predetermined area to be scanned, so as to obtain scanning data; a tomographic image acquisition unit, adapted for reconstructing a tomographic image based on the scanning data; a projection processing unit, adapted for performing, at a predetermined positioning angle, a parallel beam projection on the tomographic image by using a virtual parallel X-ray beam, so as to obtain projection data; and a pilot image re-binning unit, adapted for re-binning a CT pilot image at the predetermined positioning angle based on the projection data.

In some embodiments, the pilot image re-binning unit may include: a compositing unit, adapted for compositing an image based on the projection data to obtain a composited image; and a determining unit, adapted for defining the composited image as the CT pilot image.

In some embodiments, the pilot image re-binning unit may further include: a first denoising unit, adapted for performing a denoising process on the composited image to obtain a denoised image; wherein the determining is adapted for defining the denoised image as the CT pilot image.

In some embodiments, the CT device may further include: a second denoising unit, adapted for, after the helical scan is performed on a predetermined area to be scanned and the scanning data is obtained, performing a denoising process on the obtained scanning data to obtain denoised scanning data, and defining the denoised scanning data as a basis for reconstructing the tomographic image.

In embodiments of the present disclosure, a helical scan is adopted to scan a scanning object. Scanning data at any positioning angle can be obtained by the helical scan. A tomographic image is reconstructed based on the scanning data. Then, at a predetermined positioning angle, a parallel beam projection is performed on the tomographic image to obtain projection data of each tomographic image. A pilot image at the predetermined positioning angle is obtained based on the projection data. The parallel beam projection can eliminate geometric distortions of the pilot image. Therefore, the obtained pilot image can reflect the actual structure of the scanning object clearer and more accurate.

BRIEF DESCRIPTION OF THE DRAWINGS

In order to clarify embodiments of the present disclosure or the prior art, drawings used in the embodiments of the present disclosure or the prior art are briefly described. It should be understood that, the drawings described below are only embodiments of the present disclosure. Various changes may be made by those skilled in the art, without departing from the spirit or scope of the disclosure.

DETAILED DESCRIPTION

In order to clarify the objects, characteristics and advantages of the disclosure, the embodiments of the present disclosure will be described in detail in conjunction with the accompanying drawings. The disclosure will be described with reference to certain embodiments. It will be understood by those skilled in the art that various changes may be made without departing from the spirit or scope of the disclosure. Accordingly, the present disclosure is not limited to the embodiments disclosed.

Figure 1:
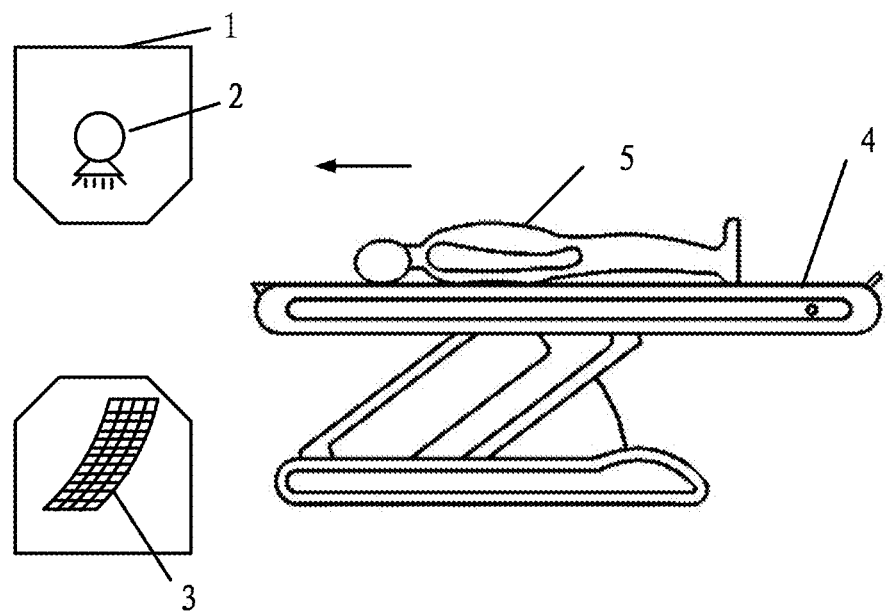
FIG. 1 illustrates a schematic diagram of pilot scan in the prior art.

As shown in FIG. 1, in the pilot image scanning method, X-rays emitted by the X-ray tube are fan shaped, and constitute a beam having a certain thickness. Because the X-rays are not parallel but the detector has an arc shape, it cannot be ensured that each X-ray irradiated on the detector is perpendicular to the plane of the detector, which results in an energy deviation between the received X-rays and the emitted X-rays. In addition, when the X-rays penetrate the scanning object and encounter obstacles, diffraction and other physical phenomenon may occur based on X-ray's own property. Because different mediums may cause different effects on the X-rays, data received by the detector also has a deviation. A CT device in the conventional art only scans at a single angle, which may result in geometric distortion in obtained pilot images because of the reasons mentioned above. Therefore, a CT pilot image acquisition method is provided in this disclosure to solve the problem.

Figure 2:
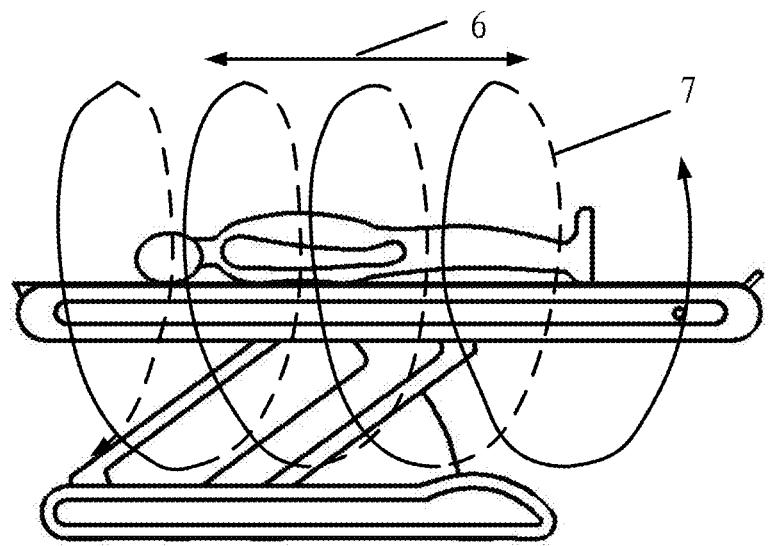
FIG. 2 illustrates a schematic diagram of pilot scan according to one embodiment of the present disclosure.

First, referring to FIG. 2, a schematic diagram of pilot scan according to an embodiment of the present disclosure is illustrated. Helical scan is adopted in the embodiment. As shown in FIG. 2, a scanning trajectory indicated by a number "6" is adopted in the prior art, while a scanning trajectory indicated by a number "7" is adopted in the present disclosure. As shown in FIG. 2, the helical scan trajectory is adopted in the embodiment of the present disclosure, which means the X-ray tube and the detector are not static, but have a helical trajectory. Embodiments of the present disclosure are described based on the schematic diagram of pilot scan shown in FIG. 2. As shown in Table 1, in order to facilitate the description of embodiments, a plurality of parameters for describing embodiments of the present disclosure are defined in Table 1.

TABLE 1 parameters and definition

| Parameter Name | Definition |
|---|---|
| $f(x', y')$ | low-dose tomographic image |
| $\beta$ | projection angle |
| $I_p(\beta, S')$ | projective result |
| O | scanning center |
| $x$ | x-coordinate data of pixel (with respect to the scanning center) |
| y | y-coordinate data of pixel (with respect to the scanning center) |
| M | moving distance of the patient table in a helical scan circle |
| $N_s$ | slice number of an X-ray detector |
| $\Delta s$ | width of each slice of an X-ray detector |
| P | pitch $P = \dfrac{M}{N_s \times \Delta s}$, where $N_s$ represents a slice of an X-ray detector, $\Delta s$ represents a width of each slice of an X-ray detector |
| L | scanning length |
| $I_{mA}$ | scanning current (mA) |
| R | distance from a point of a X-ray to the center point of the X-ray |
| S | distance from a X-ray to a center X-ray |
| T | scanning time |
| t | rotation time of a gantry |
| D | X-ray dose (mAs) |
| $R_{Max}$ | maximum distance from a point to a center point on a projection optical path |

Figure 3:
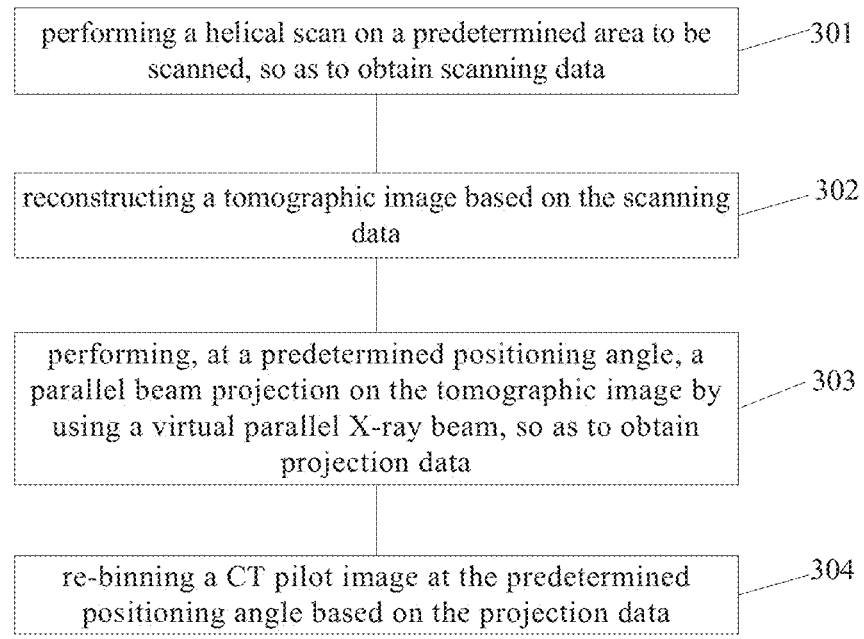
FIG. 3 illustrates a schematic flow chart of a CT pilot image acquisition method according to one embodiment of the present disclosure.

Referring to FIG. 3, FIG. 3 illustrates a schematic flow chart of CT pilot image acquisition method according to one embodiment of the present disclosure. The method may include the steps of 301, 302, 303 and 304.

In step 301, a helical scan is performed on a predetermined area to be scanned to obtain scanning data.

In practice, a scanning area is predetermined before the helical scan. Taking a lesion area (such as a heart are as an example, the scanning area is determined to be the heart area in a range of 40 centimeters from the neck. In the process of helical scan, the helical scan is performed in the range of the scanning area to obtain the scanning data. When X-rays are adopted to scan, energy of the emitted X-rays is known. When the X-rays penetrate a scanning object, absorption of the X-rays is different in different parts of the scanning object, so that energy received by the detector is different at different positions. The X-ray energy received by the detector is the scanning data in this disclosure.

Preferably, according to one embodiment, when the X-ray tube and the detector rotates around the scanning object at a constant speed, the patient table, which carries the scanning object, may move along the horizontal direction to cover the scanning area, so as to obtain the scanning data. The moving direction of the patient table may be a forward direction or a backward direction. It should be understood that, the scanning method may be adjusted according to actual needs, which is not limited in the present disclosure. In the exampled scanning mode of the present disclosure, scanning time may be expressed as Equation (1):

$$T = \frac{L}{M} \times t \qquad \text{Equation (1)}$$

According to one embodiment, if taking $I_{mA}$ as a current of the X-ray tube to generate X-rays, a required X-ray dose D may be expressed as Equation (2):

$$D = I_{mA} \times T \qquad \text{Equation (2)}$$

According to Equation (1) and Equation (2), a main fact impacting the X-ray dose is the scanning time T. In order to shorten the scanning time T and reduce the X-ray dose, a large pitch scan should be adopted, which means the pitch P should be greater than 1. Similarly, the current $I_{mA}$ of the X-ray tube should be reduced as much as possible, as long as the image quality can meet practical requirements. P and $I_{mA}$ should be determined under the premise that the X-ray dose is not greater than a scanning X-ray dose in an original pilot image, where the original pilot image is a pilot image obtained with conventional methods.

In one embodiment, the scanning may be performed with a low dose and a large pitch, where the large pitch is larger than 1. In some embodiments, the pitch may be less than 1 in practical application. The X-ray dose for obtaining pilot image may be different when different pitches are adopted. The pitch may be adjusted according to practical application environment, and is not limited in the present disclosure. Besides, as long as the image quality can meet practical requirement, an irradiation time, during which the scanning object receives the X-ray, may be reduced by increasing the rotation speed of the gantry and the slice number of the detector. Under the premise that the scanning time is short enough, the X-ray dose in embodiments of this disclosure may be close to an X-ray dose in a normal pilot image by increasing the rotation speed of the gantry and the slices of the detector, where the normal pilot image is a pilot image obtained with conventional methods.

In step 302, a tomographic image is reconstructed based on the scanning data.

Conventional methods for tomographic image reconstruction may be adopted to reconstruct the tomographic image based on the scanning data. The image reconstruction method is not the focus of the present disclosure, so it is not described in detail herein. In one embodiment, a thickness of the tomographic image and a distance between two adjacent tomographic images may be adjusted according to actual needs.

In step 303, at a predetermined positioning angle, a parallel beam projection is performed on the tomographic image by using a virtual parallel X-ray beam, so as to obtain projection data.

Figure 4:
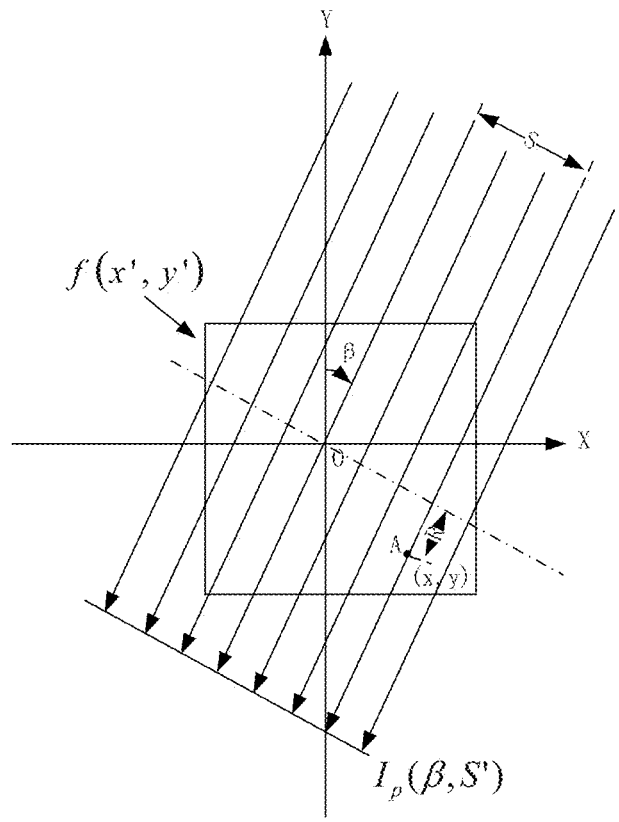
FIG. 4 illustrates a schematic diagram of projection according to one embodiment of the present disclosure.

By performing a projection on the tomographic image reconstructed in step 302, pilot images at any projection angle can be obtained in this step, where the projection angle means the positioning angle. The projection is a process to simulate the X-ray penetrating an image area to obtain projection data, under the condition that the tomographic image has been reconstructed. Because non-parallel X-ray beams may affect the accuracy of the pilot image, the virtual parallel X-ray beam is adopted to perform a parallel beam projection on the tomographic image, so as to obtain an accurate result. Referring to FIG. 4, FIG. 4 illustrates a schematic diagram of the parallel beam projection. As shown in FIG. 4, a dot line is perpendicular to the direction of the parallel X-ray beam, and passes through the scan center "O"; and f(x',y') is the tomographic image. For any point, such as a point A, on any X-ray of the parallel beam projection, the X-ray, on which the point A is, may be expressed as an equation shown below:

$$y' = x' ctg\beta + S$$

According to the equation of the X-ray on which the point A is, spatial coordinates corresponding to the point A may be expressed as equations shown below:

$$\begin{cases} x = S\cos\beta - R\sin\beta \\ y = S\sin\beta + R\cos\beta \end{cases}$$

Figure 5:
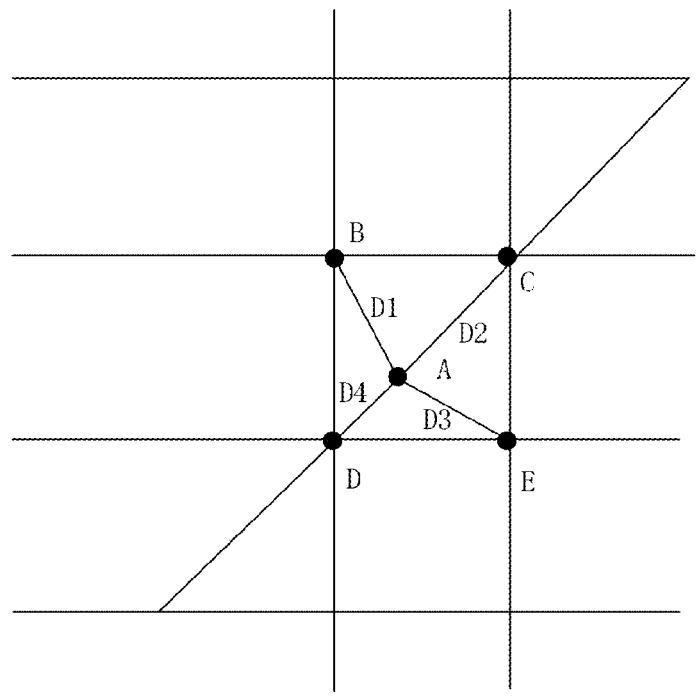
FIG. 5 illustrates a schematic diagram for obtaining a projection pixel value of a X-ray according to one embodiment of the present disclosure.

After obtaining the spatial coordinates of the point A, pixel value of the point A may be calculated. Referring to FIG. 5, FIG. 5 illustrates a schematic diagram for obtaining spatial coordinates of the point A. The tomographic image includes a plurality of grids. After obtaining the spatial coordinates of the point A, four known points (four pixels close to the point A, but the number of the points is not limited to four) is determined in four adjacent areas corresponding to the point A. Assuming that the four determined points are B, C, D and E respectively, pixel values corresponding to B, C, D and E are $f_B(x_B,y_B)$, $f_C(x_C,y_C)$, $f_D(x_D,y_D)$, and $f_E(x_E,y_E)$ respectively. Distances from the four points to the point A are D1, D2, D3 and D4 respectively. Different weights are set based on the distances from the four points to the point A. The larger the distance is, the smaller the weight is. Pixel value $f_A(x_A,y_A)$ of the point A, referring as $P_R(S')$, is obtained with a linear interpolation method. In the range of the tomographic image, a plurality of points are selected along a X-ray on which the point A is. Pixel value of each point is calculated. The more the points are selected, the more accurate the obtained pilot image is. A projection pixel value of the X-ray, on which the point A is, is obtained by adding pixel values of the points selected on the X-ray, which may be expressed as an equation shown below:

$$I_P(\beta, S') = \sum_{R \in [-R_{Max}, R_{Max}]} P_R(S').$$

In step 304, a CT pilot image is re-binned at the predetermined positioning angle based on the projection data.

Based on the step 303, projection data of each X-ray may be obtained. Projection data of each X-ray passing through the tomographic image can constitute a "line". Because the tomographic image has a thickness, the "line" has a thickness. After projection of each tomographic image, a plurality of "lines" are obtained. Based on a sequence of the tomographic images, an image is re-binned by arranging the "lines", which is the pilot image.

In embodiments of the present disclosure, helical scanning method is adopted to scan. Scanning data at any projection angle can be obtained by helical scan. The tomographic image is reconstructed based on the scanning data. Then, at the predetermined positioning angle, the projection data of each tomographic image is obtained by performing a parallel beam projection on the tomographic images. The pilot image at the predetermined positioning angle is re-binned based on the projection data. The parallel beam projection can eliminate geometric distortions of the pilot image. Therefore, the pilot image can reflect the actual structure of the scanning object clearer and be more accurate.

Compared to the conventional art, images obtained in embodiments of the present disclosure are not a pilot image at a single angle. Different pilot images are obtained at different positioning angle. It should be noted that, if the dose of the X-ray is greater, the penetration ability of the X-ray is stronger when the X-ray passes through the scanning object, and the result is more accurate. Based on the embodiment mentioned above, under a premise of a low X-ray dose, the value of $I_{mA}$ adopted in scanning process is generally far lower than that of helical scan in other application. Therefore, the scanning data has a great deal of noise. If the scanning data obtained in the step 301 is directly processed, the quality of the tomographic image may be affected by the noise. For example, the quality of the pilot image may be adversely affected by image edge blur.

Therefore, after the scanning data is obtained, a noise smoothing process is performed on the scanning data which has a great deal of noise. Specifically, the noise smoothing process may include: analyzing a cause and characteristics of noises of the scanning data; and performing an adaptive suppression based on the characteristics of the noise to reduce the impact of noise on the tomographic image. A frequency division method is used to divide the tomographic image into multi-frequency images. Then, noise suppression and edge protection are performed based on different characteristics of the noises at different frequencies, so that a tomographic image suitable for parallel beam projection is obtained.

After pilot image is obtained, a plurality of operations, such as cutting, translation, noise suppression, edge enhancement, etc, may be performed on the pilot image obtained after the parallel beam projection so as to obtain a higher quality pilot image.

In addition, in embodiments of the present disclosure, helical scan is adopted to obtain the pilot image. The method for obtaining pilot images at different projection angle can provide a basis for adjusting X-ray dose in a low dose scanning with an X-ray tube. Taking the low dose scan in the conventional art as an example, in the transition from a front side scan to a lateral side scan, an X-ray dose, corresponding to an angle between the front side and the lateral side, is calculated. Specifically, the X-ray dose is obtained based on an interpolation operation on a dose corresponding to the front side scan and a dose corresponding to the lateral side scan. However, the X-ray doses corresponding to different angles obtained by calculation cannot provide a good dose reference to an actual scan. In addition, the X-ray dose obtained by calculation is always great in practical application. However, in embodiments of the present disclosure, the scanning object is scanned at any angles, so that optimal doses for scanning at different angles can be provided by acquiring quality of the pilot image. Therefore, for the dose adjustment of the X-ray tube in subsequent steps, pilot images obtained by this method can achieve a low dose scan, and provide more accurate dose reference information.

Figure 6:
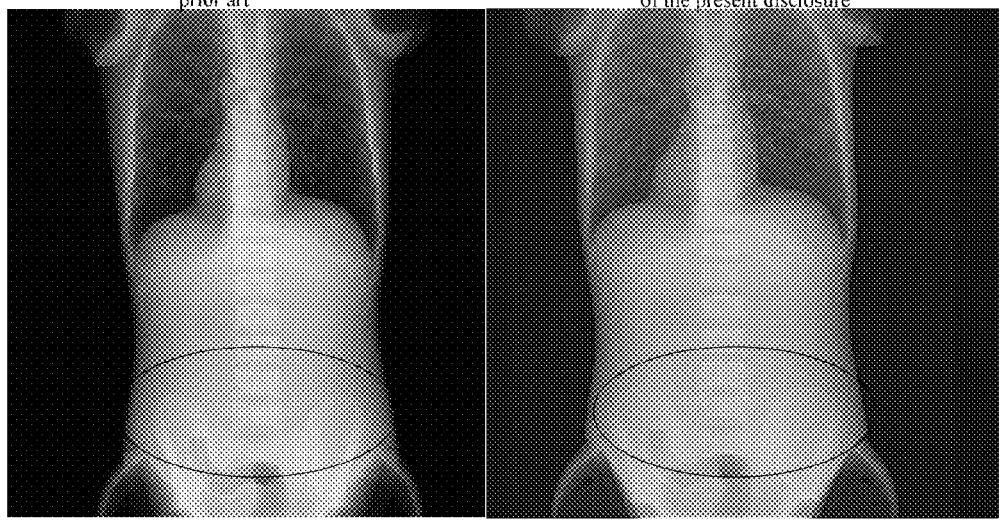
FIG. 6 schematically illustrates a pilot image obtained in the prior art and a pilot image obtained with a CT pilot image reconstruction method according to one embodiment of the present disclosure.

Referring to FIG. 6, for a same scanning object and a same scanning area, an original pilot image obtained in the conventional art and a pilot image obtained in embodiments of the present disclosure are illustrated. The portions defined by the ellipses in FIG. 6 are supposed to be symmetric, but the portion defined by the ellipse in the original pilot image obtained in the conventional art is significant distorted. While the pilot image obtained in embodiments of the present disclosure is clearer, and has no geometric distortion.

Figure 7:
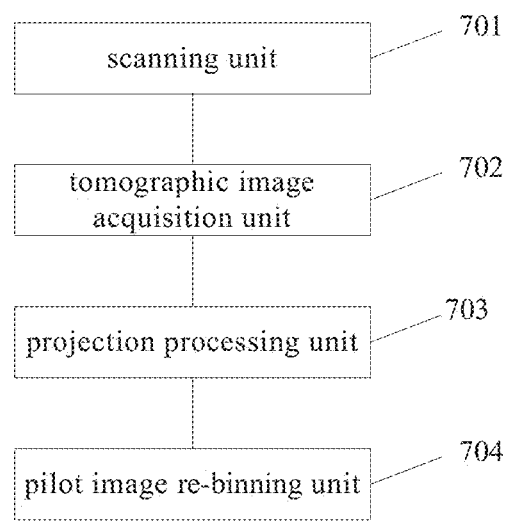
FIG. 7 illustrates a schematic structural diagram of a CT device according to one embodiment of the present disclosure.

Corresponding to the CT pilot image acquisition method described above, a CT device is provided in embodiments of the present disclosure. Referring to FIG. 7, a schematic structural diagram of a CT device is illustrated according to one embodiment. The device may include:

a scanning unit 701, adapted for performing a helical scan on a predetermined area to be scanned, so as to obtain scanning data;

a tomographic image acquisition unit 702, adapted for reconstructing a tomographic image based on the scanning data;

a projection processing unit 703, adapted for performing, at a predetermined positioning angle, a parallel beam projection on the tomographic image by using a virtual parallel X-ray beam, so as to obtain projection data; and a pilot image re-binning unit 704, adapted for re-binning a CT pilot image at the predetermined positioning angle based on the projection data.

Preferably the pilot image re-binning unit 704 may include:

a composition unit, adapted for compositing an image based on the projection data to obtain a composited image; and a determining unit, adapted for defining the composited image as the CT pilot image.

Preferably, the pilot image re-binning unit 704 may further include:

a first denoising unit, adapted for performing a denoising process on the composited image to obtain a denoised image, wherein the determining unit is adapted for defining the denoised image as the CT pilot image.

Preferably, after the scanning data is obtained, the pilot image re-binning unit 704 may further include: a second denoising unit, adapted for, after the helical scan is performed on a predetermined area to be scanned and the scanning data is obtained, performing a denoising process on the obtained scanning data to obtain denoised scanning data, and defining the denoised scanning data as a basis for reconstructing the tomographic image.

Functions of the units, achieved in embodiments of the CT device, are corresponding to the steps in embodiments of the CT pilot image acquisition method. The functions are not described in detail herein.

It should be noted that, the terms "comprise", "include" and the like in the description and in the claims, are used for covering non-exclusive inclusion. Processes, methods, objects or devices are intended to include not only the described elements, but also other elements which are not described, and inherent elements the processes, methods, objects or devices have in the absence of more restrictive conditions, elements limited by a term "include a" are not intended to exclude other similar elements included in the processes, methods, objects or devices.

Since the system embodiments are basically corresponding to the method embodiments, relevant parts of the system can refer to the method embodiments. The system is described with reference to certain embodiments in this disclosure. Units which are described as separated components may or may not be physically separated. Components described as units may or may not be physical units, that is, they may be disposed on a same place or distributed in a plurality of network cells. The purpose of the present disclosure may be realized by selecting some of all of the units according to practical requirements. Embodiments of the present disclosure can be understood and implemented by those skilled in the art without departing from the spirit or scope of the disclosure.

Although the present disclosure has been disclosed above with reference to preferred embodiments thereof, it should be understood by those skilled in the art that various changes may be made without departing from the spirit or scope of the disclosure. Accordingly, the present disclosure is not limited to the embodiments disclosed.

What is claimed is:

1. A Computed Tomography (CT) pilot image acquisition method, comprising:
performing a helical scan on a predetermined area to be scanned, so as to obtain scanning data;
reconstructing a tomographic image based on the scanning data;
performing, at a predetermined positioning angle, a parallel beam projection on the tomographic image by using a virtual parallel X-ray beam, so as to obtain projection data; and
re-binning a CT pilot image at the predetermined positioning angle based on the projection data.

2. The method according to claim 1, wherein re-binning a CT pilot image at the predetermined positioning angle based on the projection data, comprising:
compositing an image based on the projection data to obtain a composited image; and
defining the composited image as the CT pilot image at the predetermined positioning angle.

3. The method according to claim 2, further comprising:
performing a denoising process on the composited image to obtain a denoised image; and
defining the denoised image as the CT pilot image at the predetermined positioning angle.

4. The method according to claim 1, further comprising:
after the helical scan is performed on a predetermined area to be scanned and the scanning data is obtained, performing a denoising process on the scanning data to obtain denoised scanning data, and defining the denoised scanning data as a basis for reconstructing the tomographic image.

5. The method according to claim 1, wherein a thickness of the tomographic image is adjustable; and
wherein a plurality of tomographic images are reconstructed based on the scanning data, and a distance between adjacent tomographic images is adjustable.

6. The method according to claim 1, wherein a pitch adopted in performing the helical scan on the predetermined area to be scanned, is adjustable.

7. A CT device, comprising:
a scanning unit, adapted for performing a helical scan on a predetermined area to be scanned, so as to obtain scanning data;
a tomographic image acquisition unit, adapted for reconstructing a tomographic image based on the scanning data;
a projection processing unit, adapted for performing, at a predetermined positioning angle, a parallel beam projection on the tomographic image by using a virtual parallel X-ray beam, so as to obtain projection data; and
a pilot image re-binning unit, adapted for re-binning a CT pilot image at the predetermined positioning angle based on the projection data.

8. The CT device according to claim 7, wherein the pilot image re-binning unit comprises:
a compositing unit, adapted for compositing an image based on the projection data to obtain a composited image; and
a determining unit, adapted for defining the composited image as the CT pilot image.

9. The CT device according to claim 8, wherein the pilot image re-binning unit further comprises:
a first denoising unit, adapted for performing a denoising process on the composited image to obtain a denoised image;
wherein the determining unit is adapted for defining the denoised image as the CT pilot image.

10. The CT device according to claim 9, further comprising:
a second denoising unit, adapted for, after the helical scan is performed on a predetermined area to be scanned and the scanning data is obtained, performing a denoising process on the scanning data to obtain denoised scanning data, and defining the denoised scanning data as a basis for reconstructing the tomographic image.

* * * * *